United States Patent
Terpilowski et al.

(10) Patent No.: US 6,234,993 B1
(45) Date of Patent: May 22, 2001

(54) LOW PROFILE PHACO HANDPIECE

(75) Inventors: Ed Terpilowski, Redmond; Robert F. Jordan, Brier; Lawrence Laks, Bellevue; Timothy E. Luxon, Kirkland, all of WA (US)

(73) Assignee: MicroSurgical Technology, Inc., Redmond, WA (US)

( * ) Notice: Subject to any disclaimer, the term of this patent is extended or adjusted under 35 U.S.C. 154(b) by 0 days.

(21) Appl. No.: 09/434,759

(22) Filed: Nov. 4, 1999

(51) Int. Cl.[7] .................................................... A61M 1/00
(52) U.S. Cl. ................................................ 604/35; 604/43
(58) Field of Search .................... 604/43, 44, 45, 604/164, 22, 35, 523, 526, 532, 533, 534, 535, 537, 538, 284, 173, 96–102, 271, 272; 606/167, 169, 170, 171, 185, 107; 601/2

(56) References Cited

U.S. PATENT DOCUMENTS

| | | | |
|---|---|---|---|
| 883,583 | * 3/1908 | Stallsmith | 604/43 |
| 1,114,268 | * 10/1914 | Kells | 604/43 |
| 3,495,595 | * 2/1970 | Soper | 604/43 |
| 4,955,375 | * 9/1990 | Martinez | 604/43 |
| 5,084,013 | * 1/1992 | Takase | 604/43 |
| 5,219,335 | * 6/1993 | Willard et al. | 604/164 |
| 5,318,517 | * 6/1994 | Reiman | 604/43 |
| 5,843,109 | * 12/1998 | Mehta et al. | 606/169 |
| 5,984,889 | * 11/1999 | Christ et al. | 604/22 |

* cited by examiner

*Primary Examiner*—Manuel Mendez
(74) *Attorney, Agent, or Firm*—Christensen O'Connor Johnson Kindness PLLC

(57) ABSTRACT

A passage for irrigation liquid extends lengthwise along the exterior surface of the body of a phacoemulsifier handpiece and is formed between an outer arcuate section and the exterior surface of the body itself. The passage is of non-circular cross section so that it protrudes from the body, but to a lesser degree than a circular conduit having the same cross-sectional area.

4 Claims, 2 Drawing Sheets

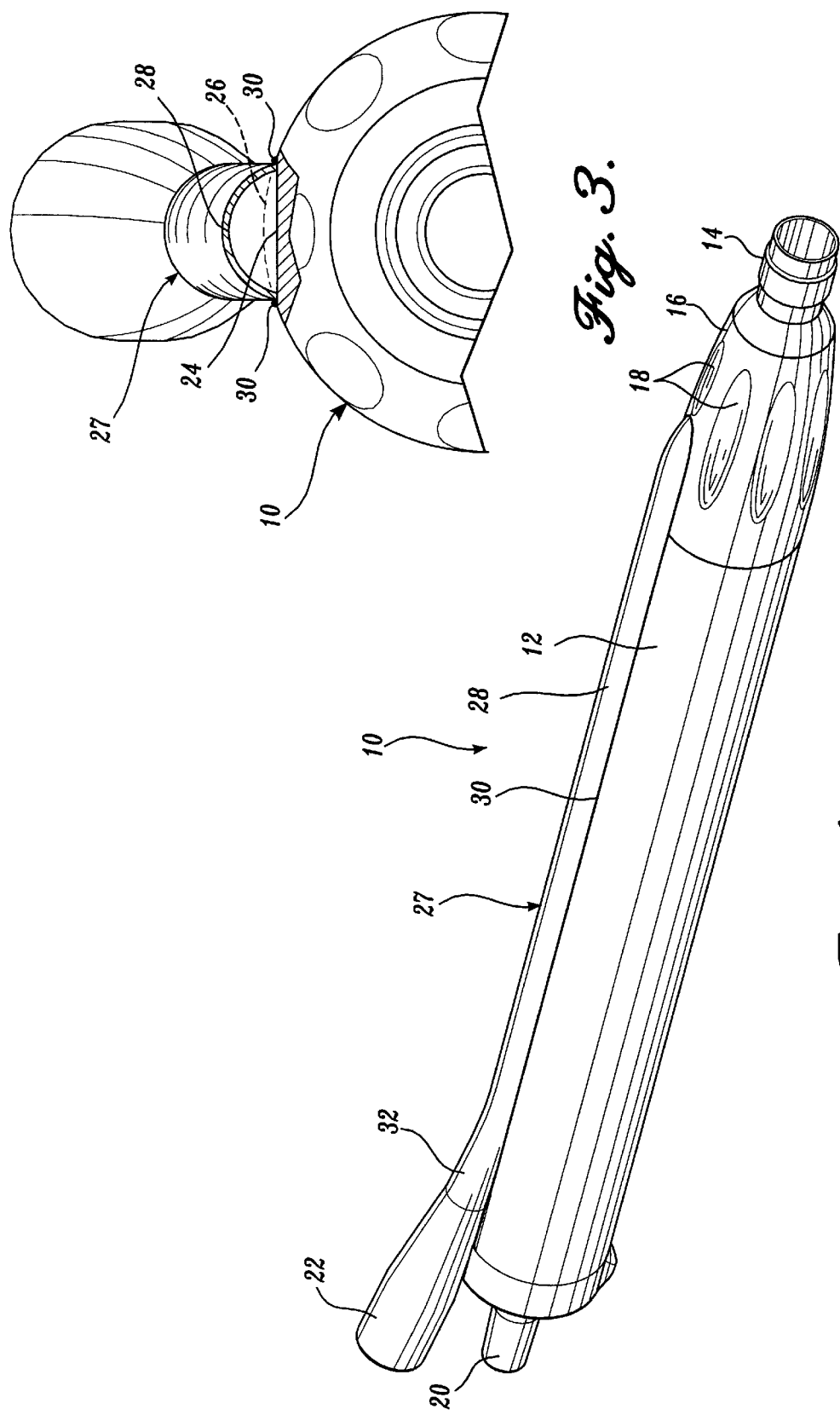

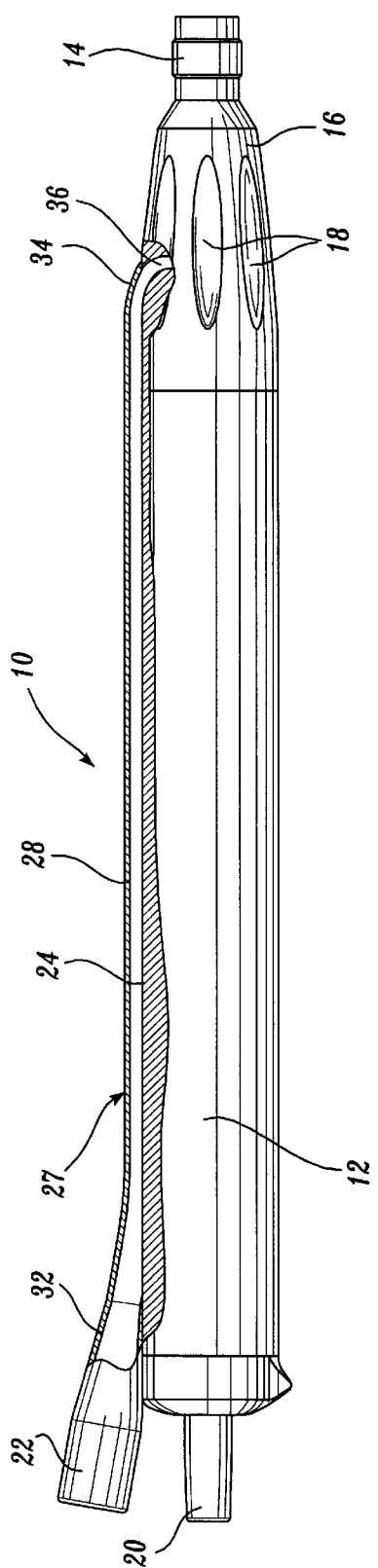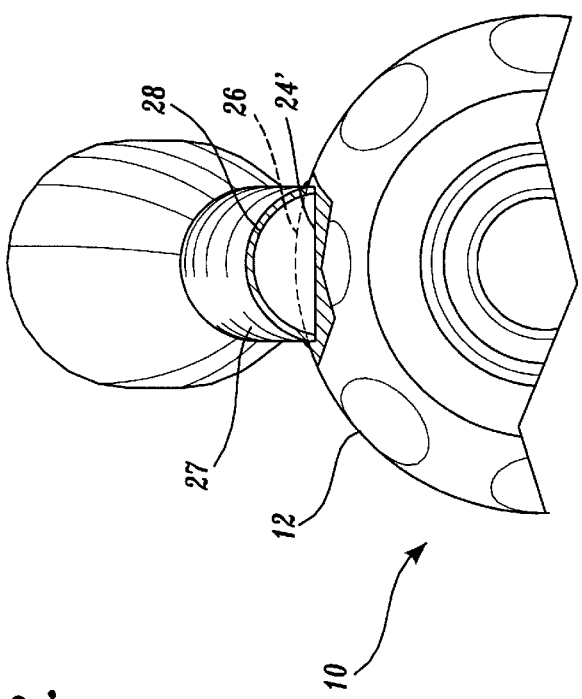

LOW PROFILE PHACO HANDPIECE

FIELD OF THE INVENTION

The present invention relates to surgical devices, in particular to phacoemulsifiers and irrigation-aspiration tools for removing phaco-emulsified lenses and cleaning the lens capsule.

BACKGROUND OF THE INVENTION

One of the more common afflictions to affect aging eyes are cataracts, which cause gradually deteriorating vision. Advances in ophthalmic surgery allow many cataracts to be removed and vision restored.

Treating cataracts typically involves the removal of the clouded natural lens and replacement with an artificial lens. Removal of the lens requires an incision or tunnel to be made in and/or adjacent to the cornea and a phaco-emulsifier needle or tip to be inserted into the eye. The phacoemulsifier tip vibrates ultrasonically to break up or liquefy the lens. The emulsified lens is removed from the eye by aspiration, and the artificial lens is then inserted.

Modern phacoemulsifiers and aspirators have long but narrow cylindrical tips with coaxial passages. Aspiration typically is through a central passage of circular cross section. Simultaneously, irrigation is through an annular passage encircling the aspiration passage. In the typical arrangement, the central, circular aspiration passage extends axially of the phacoemulsifier handpiece for connection to an external vacuum source. The irrigation liquid is conveyed from an external source through a conduit that enters the distal end of the handpiece, near the tip. Both external sources are connected to the handpiece by flexible tubes, so that the handpiece can be manipulated during the phacoemulsifying and cleansing procedures.

SUMMARY OF THE INVENTION

The present invention provides an improved handpiece for a phacoemulsifier or irrigator-aspirator instrument. Similar to known instruments, the handpiece includes a long, substantially cylindrical body with standard connectors at the proximal end for flexible conduits leading to a vacuum source and a source of irrigation liquid. In accordance with the present invention, the irrigation liquid is conveyed along a low profile passage formed between an upper arcuate conduit section and a preferably flat top section of the handpiece body. Water tight integrity of the irrigation passage is achieved by laser welding the arcuate top conduit section to the body of the handpiece. Preferably, the outer periphery of the composite irrigation passage projects beyond the profile of the cylindrical body, but not to as a great a degree as a circular passage of the same cross-sectional area, and with a more gentle transition from the body than for a circular cross-section conduit extending along the body. The composite irrigation passage extends almost the full length of the handpiece and provides convenient tactile recognition to the surgeon of the rotated position of the handpiece. Nevertheless, the lower profile afforded by the noncircular passage allows the instrument to be rotated in the hand as necessary for a desired alignment of a phaco tip, for example, without unduly interfering with the fit and grasp of the instrument in the hand.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 is a top front perspective of a low profile phaco handpiece in accordance with the present invention.

FIG. 2 is a side elevation of the handpiece of FIG. 1, with parts broken away.

FIG. 3 is an enlarged fragmentary front-end elevation of the handpiece of FIG. 1 with parts broken away.

FIG. 4 is an enlarged fragmentary front end elevation of a second embodiment of a low profile phaco handpiece in accordance with the present invention.

DETAILED DESCRIPTION OF THE PREFERRED EMBODIMENT

As described above, the most common treatment for cataracts is to emulsify the clouded natural lens, aspirate the lens from the eye and replace the lens with an artificial lens. With reference to FIG. 1, a phacoemulsifying instrument 10 typically includes a long cylindrical body 12 containing an ultrasonic engine and electronics to vibrate a phaco tip (not shown) attached to the distal end 14 of the body. Moving proximally from the tip 14, the body has a tapered nose section 16 with regularly spaced ribs, grooves or recesses 18 for convenient grasping and manipulation of the tool by the surgeon. The dimensions of the nose 16 are such that the surgeon's fingers engage the nose, whereas the longer cylindrical portion of the body 12 fits within the hand. A source of vacuum is connected at a central rear port 20, and a source of irrigation fluid is connected at a port 22.

In conventional designs, the conduit from the irrigation port 14 enters the body of the instrument close to the tip 14, or at least in the area of the nose portion 16. In known constructions, the conduit for the irrigation fluid is of circular cross section. It may extend at an angle into the body, or substantially radially into the body, or lengthwise along the top of the cylindrical body. In the latter case, there is a circular conduit secured over the circular body.

One advantage of a long conduit extending along the body is to provide a tactile reference for the surgeon as to the rotated position of the instrument. Sometimes the phaco tip will have a beveled end, and the position of the bevel can be gauged by the position of the conduit. Nevertheless, the conduits can interfere with or impede manipulation of the instrument due to the abrupt projection of the conduit from the body of the handpiece.

With reference to FIG. 2 and FIG. 3, in accordance with the present invention a long axially extending portion 24 of the outer shell of the body 12 is flattened, which can be achieved by machining after the tip 14 nose 16 and body 12 have been assembled. This section 24 is located radially inward from the profile of the cylindrical body, indicated by the broken line 26 in FIG. 3, and therefore is referred to as being "recessed" into the body. The irrigation conduit 27 of the handpiece in accordance with the present invention has a noncircular, preferably approximately semicircular top segment 28 with a maximum diameter (in a horizontal direction as viewed in FIG. 3) of approximately the same extent as the flattened or recessed portion 24 of the body. The top segment 28 is secured to the body by a continuous, water tight, laser weld bead 30.

The rear end portion 32 of the irrigation conduit 26 is bent upward to a tubular section of circular cross section. The tubular portion forms the fitting 22 for coupling to a flexible tube leading to the source of irrigation fluid. The leading or distal end 34 of the irrigation conduit curves downward to the nose 16 of the handpiece. In this area, the handpiece includes an internal duct or manifold 36, leading to the tip 14 of the handpiece through which the irrigation fluid is expelled.

The top segment 28 of the irrigation conduit can be formed by first shaping a tube of circular cross section with the long and straight central section, downward bent distal section, and upwardly bent proximate section. This tube is cut along the axis of the long and straight central section, thereby forming the open bottomed shell which is secured to the body 12 of the handpiece as described above.

In the preferred embodiment, the top section 24 of the body over which the segment 28 fits is formed by machining a flat section into the body. Alternatively, as shown in FIG. 4, a shallow groove or notch 24' may be cut lengthwise into the body, for reception of the opposite bottom margins of the segment 28. This further reduces the profile of the irrigation conduit at the top. Nevertheless, the conduit does protrude beyond the normal periphery of the cylindrical body 12 so that it provides a convenient and accurate reference for the rotational orientation of the handpiece in the hand of a surgeon.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A surgical handpiece comprising an elongated generally cylindrical body for grasping by a user, the elongated body including an outer shell having a lone axially extending exterior portion, such exterior portion being flattened, and a fluid-conducting conduit extending lengthwise along the body, the conduit being of noncircular cross-section and having an outer segment formed separately from the body, the outer segment having opposite side edges each secured water tight to the flattened exterior portion of the outer shell of the body, the conduit outer segment protruding from the body, and the segment and body defining a fluid passage between the flattened exterior portion of the outer shell of the body and the outer conduit segment.

2. The surgical handpiece defined in claim 1 in which the fluid passage is of approximately semicircular cross section.

3. The surgical handpiece defined in claim 1 in which the flattened exterior portion of the outer shell of the body is a groove in the exterior surface of the body, the outer conduit segment being arcuate and having opposite margins closely received in the groove and secured within the groove.

4. The surgical handpiece defined in claim 3, in which the outer conduit segment is approximately semicircular.

* * * * *

UNITED STATES PATENT AND TRADEMARK OFFICE
CERTIFICATE OF CORRECTION

PATENT NO.   : 6,234,993 B1
DATED        : May 22, 2001
INVENTOR(S)  : E. Terpilowski et al.

It is certified that error appears in the above-identified patent and that said Letters Patent is hereby corrected as shown below:

Column 4,
Line 3, "elongated" should read -- elongated, --
Line 5, "lone" should read -- long --

Signed and Sealed this

Eighth Day of January, 2002

Attest:

JAMES E. ROGAN
Attesting Officer    Director of the United States Patent and Trademark Office